United States Patent [19]
Girard et al.

[11] Patent Number: 5,928,415
[45] Date of Patent: *Jul. 27, 1999

[54] SELECTION DEVICE FOR PROVIDING ONE OR THE OTHER OF TWO GASES TO AN APPARATUS

[75] Inventors: Jean-Marc Girard, Paris; Alain Mail, Domene; Yves Marot, Buc, all of France

[73] Assignee: L'Air Liquide, Societe Anonyme pour l'Etude et l'Exploitation des Procedes Georges Claude, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/752,071

[22] Filed: Nov. 19, 1996

[30] Foreign Application Priority Data

Nov. 5, 1996 [FR] France .................................. 96 13435

[51] Int. Cl.$^6$ .................................................. B01D 53/22
[52] U.S. Cl. .................................... 96/4; 96/110; 96/113; 96/397; 96/417
[58] Field of Search ........................... 55/210, 212, 270; 96/4, 108, 110, 113, 397, 417

[56] References Cited

U.S. PATENT DOCUMENTS

| Re. 34,434 | 11/1993 | Campbell et al. | 55/270 X |
|---|---|---|---|
| 3,501,899 | 3/1970 | Allen | 55/210 |
| 3,638,401 | 2/1972 | Kabler | 55/270 X |
| 3,976,450 | 8/1976 | Marcote et al. | 55/270 X |
| 4,293,316 | 10/1981 | Block | 55/270 X |
| 4,385,910 | 5/1983 | Eilers et al. | 55/270 X |
| 4,995,889 | 2/1991 | Abel et al. | 96/113 X |
| 5,488,811 | 2/1996 | Wang et al. | 55/210 X |
| 5,496,388 | 3/1996 | Tellier | 55/210 |

FOREIGN PATENT DOCUMENTS

| 2049673 | 3/1971 | France | 55/270 |
|---|---|---|---|
| 2714968 | 7/1995 | France . | |
| WO90/09585 | 8/1990 | WIPO | 55/270 |

*Primary Examiner*—Robert Spitzer
*Attorney, Agent, or Firm*—Burns, Doane, Swecker & Mathis, L.L.P.

[57] ABSTRACT

A selection device for delivering one of two gases to an apparatus includes an apparatus having an inlet and an outlet, and a gas delivery line connected to the inlet of the apparatus. A first feed line and a second feed line for respectively feeding a first and a second gas are provided. A first purge line and a second purge line are also provided, the first feed line being connected to the first purge line and the second feed line being connected to the second purge line. A common connection line connects the first and the second feed lines to the gas delivery line. An additional purge line is connected to the outlet of the apparatus. A first element, a second element, and a third element for creating a pressure drop are disposed in the first, the second, and the additional purge lines, respectively, the first element for creating a pressure drop and the third element for creating a pressure drop being flow-regulating elements, the second element for creating a pressure drop being a backpressure regulator. The common gas delivery line is only connected to the common connection line and to the apparatus.

7 Claims, 4 Drawing Sheets

FIG.5

SELECTION DEVICE FOR PROVIDING ONE OR THE OTHER OF TWO GASES TO AN APPARATUS

BACKGROUND OF THE INVENTION

1. Field of the Invention

The invention relates to a selection device for delivering a gas emanating from one of two feed lines to an apparatus, especially a trace-impurity analyzer such as an atmospheric-pressure ionization mass spectrometer.

2. Description of Related Art

Such a selection device, designed to feed a trace-impurity analyzer either with a gas to be analyzed or with a "calibration" gas which is a pure gas or one containing impurities at precisely known concentrations, is known from Document FR-A-2714968, owned by the assignee of the present invention. The device of the aforementioned document comprises a first and a second line which feed respectively an analysis gas and a calibration gas. Each feed line emerges in a respective purge line. The feed lines for the two gases are connected to the analyzer via a line which connects the two feed lines and via a common line for delivering gas to the analyzer.

The parameters relating to introduction of the gas into the analyzer are controlled, on the one hand, using an upstream pressure regulator mounted on a discharge line connected as a bypass to the common delivery line and, on the other hand, using a flow regulator mounted on an additional purge line connected to an outlet of the apparatus.

Each purge line of the feed lines includes a mass flowmeter. These flowmeters allow selection either of the gas to be analyzed or the calibration gas. It may therefore be understood that for selecting the gas delivered to the analyzer or for controlling the parameters relating to the introduction of the gas into the analyzer, use is made of three mass flowmeters, placed in each of the purge lines, as well as an upstream pressure regulator placed in a line branched off from the common line for delivering gas to the apparatus.

The present invention aims to simplify the known device by providing a selection device which is simpler and more economic.

SUMMARY AND OBJECT OF THE PRESENT INVENTION

For this purpose, the subject of the invention is a selection device for delivering one of two gases to an apparatus, comprising a first and a second line for respectively feeding a first and a second gas, each feed line emerging in a respective purge line, and a common connection line connecting the two feed lines to a common gas delivery line connected to an inlet of the apparatus, an outlet of the apparatus being connected to an additional purge line, an element for creating a pressure drop being placed in each purge line, the element for creating a pressure drop in the purge line associated with the first feed line as well as the element for creating a pressure drop in the additional purge line being flow-regulating elements, characterized in that the element for creating a pressure drop in the purge line associated with the second feed line is a backpressure regulator and in that the common gas delivery line is only connected, on the one hand, to the connection line and, on the other hand, to the apparatus.

Other characteristics and advantages of the invention will appear from the following description given by way of example but having no limiting character, with regard to the appended drawings in which:

DETAILED DESCRIPTION OF THE PREFERRED EMBODIMENTS

Figure 1:
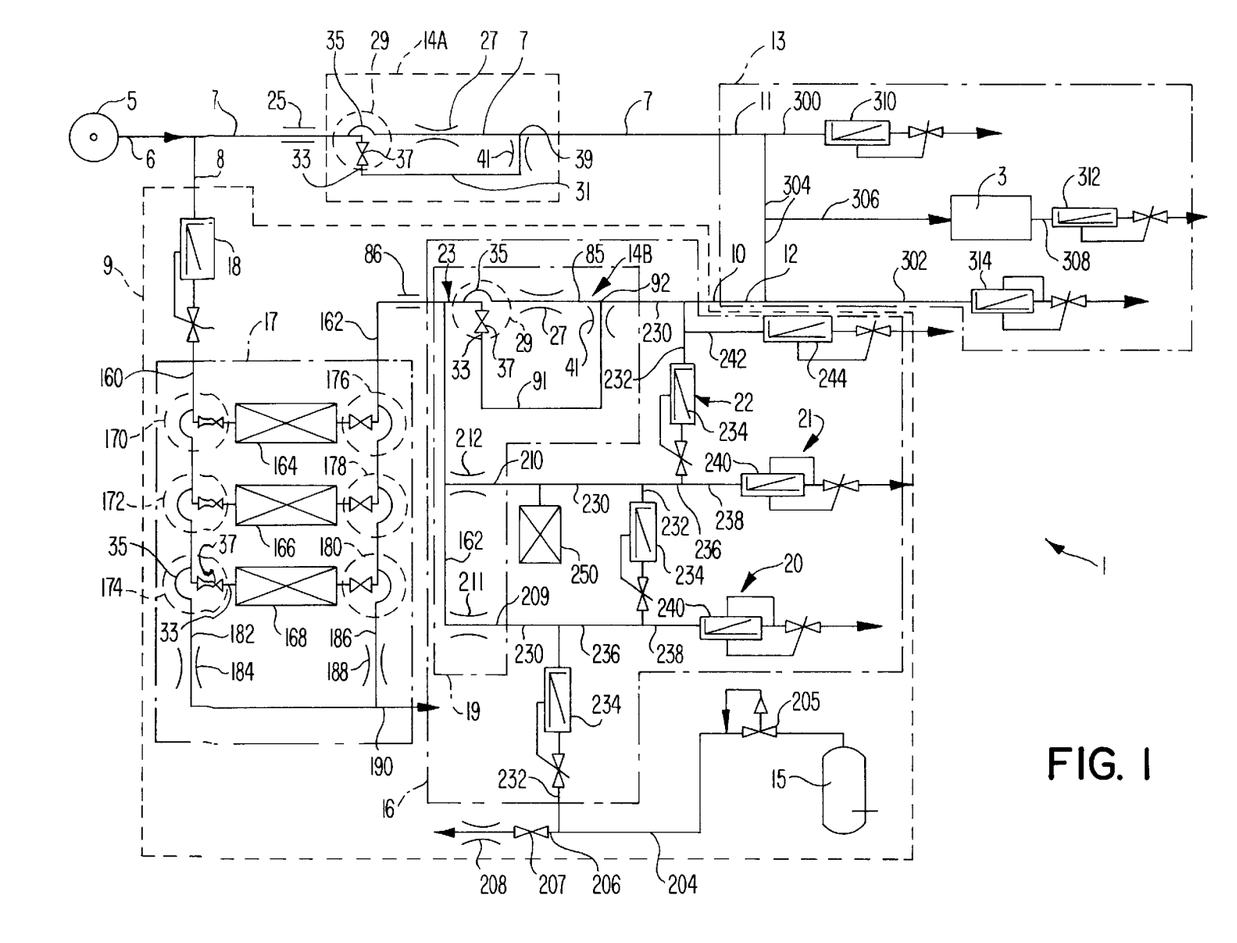
FIG. 1 is a general diagram of a plant for delivering, to an apparatus, either a gas to be analyzed or a pure gas, or else a gas charged with a predetermined quantity of impurities.

FIG. 1 shows a plant 1 for delivering gas to an apparatus 3 such as, for example, an apparatus for analyzing trace impurities in a gas, of the atmospheric-pressure ionization mass spectrometer. Such an analyzer 3 is capable of measuring trace impurities in a gas at very low concentrations of between $10^{-2}$ to $10^{-5}$ ppm, or indeed from $10^{-3}$ to $10^{-6}$ ppm. As will be explained in detail hereinbelow, this plant 1 delivers, to the apparatus 3, alternately a pure reference gas or "zero gas", that is to say a gas typically containing less than $10^{-4}$ ppm of impurities, a gas charged with a predetermined quantity of known gaseous impurities such as, for example, $H_2O$, $CO_2$, $CO$, $O_2$, $CH_4$, $H_2$, etc., at concentrations varying within a range extending for example from $10^{-5}$ ppm to $10^{-2}$ ppm, or else a gas to be analyzed. Furthermore, this plant must control the parameters relating to the introduction of the gas into the analyzer 3, such as the pressure and the flow rate.

In addition, this plant must allow the successive use of various kinds of gas to be analyzed.

For this purpose, a source 5 of a pressurized gas to be analyzed is connected via a sampling line 6 to the gas delivery plant 1. This source 5 comprises, for example, a single source of one kind of gas to be analyzed, or several pressurized sources of various kinds of gases, each connected via a sampling line to a device intended to deliver any one of the several gases to an apparatus, such as the device described in French Patent Application No. FR-960756096, owned by the assignee of the present invention and filed on Jun. 18, 1996.

The sampling line 6 is connected, on the one hand, to an analyzing line 7 and on the other hand, to a feed line 8 of a device 9 for delivering a pure gas or a gas charged with a predetermined quantity of gaseous impurities.

The analyzing line 7 and an outlet line 10 of the delivery device 9 are each connected to a corresponding inlet line 11, and 12 of a selection device 13 in order to deliver to the apparatus 3 either the gas contained in the analyzing line 7 or the gas output by the outlet line 10 of the delivery device 9.

A device 14A, for regulating a predetermined gas flow for gases to be analyzed which have substantially different molar masses, is placed in the analyzing line 7.

The delivery device 9 comprises a source of pure gas, a source 15 of impurities and means 16 of diluting the impurities in the pure gas in a predetermined manner.

The source of pure gas consists, on the one hand, of the source 5 of the gas to be analyzed and, on the other hand, of a unit 17 for purifying the gas output by the source 5, the flow of gas feeding the purification unit being controlled by means of a mass flow regulator 18 placed in the feed line 8. It will be noted that the purification unit is located advantageously downstream of the flow regulation.

The diluting means 16 include means 19 of splitting the gas flow output by the purification unit 17, which means feed several dilution stages 20, 21, 22 placed in series.

A branch 23 of the flow-splitting means 19 includes a device 14B for regulating a predetermined upstream gas pressure for gases having substantially different molar masses, the structure of this device 14B being identical to that of the regulating device 14A.

The structure and operation of the various units of the gas delivery plant 1 will be described in detail hereinbelow.

I. Device for Regulating the Flow of Gases Having Substantially Different Molar Masses I.1 Structure of the Regulating Device The regulating device 14A is placed in the analyzing line 7. Placed upstream of this regulating device 14A is a pressure gauge 25 for determining the pressure upstream of the regulating device 14A.

The regulating device 14A includes, for the embodiment shown, a gaged restriction 27, for example a gaged orifice, placed in the analyzing line 7. Placed upstream of the orifice 27 is a branching valve 29, shown diagrammatically surrounded by dashes, for the selective use of a bypass line 31.

The valve 29 comprises a first conduit 33 permanently connected via one end to the bypass line 31. It furthermore comprises a second, always-open conduit 35 which is placed in the analyzing line 7.

The first conduit 33 and the second conduit 35 of the valve 29 may be brought into communication by an actuator 37, as will be explained in detail hereinbelow, which can switch between a position for bringing the first conduit 33 into communication with the second conduit 35 and a position for isolating the first conduit 33 from the second conduit 35. The bypass line 31 is connected via its other end 39, downstream of the orifice 27, to the analyzing line 7.

A second gaged orifice 41 is advantageously placed in the bypass line 31, as close as possible to the end 39 of the latter. Thus, a flow-stagnation volume, formed in the isolating position of the two conduits 33 and 35 by that part of the bypass line 31 lying between the orifice 41 and the end 39, is as small as possible.

The structure of the regulating device 14B is identical to that of the device 14A. This is why the identical elements bear the same reference numbers.

This device thus includes a first orifice 27 placed in a feed line 85 for a pure gas output by the purification unit 17. Placed in this line 85 is a branching valve 29 identical to that of the device 14A. Connected to the conduit 33 of the valve 29 is one end of a bypass line 91. The other end of this line 91 is joined downstream of the orifice 27 to the feed line 85. A gaged orifice 41 is placed as close as possible to the end 92 via which the bypass line 91 is joined to the feed line 85.

I.2. Structure of the Valve of the Regulating Devices

An embodiment example of the valve 29 fitted in the regulating devices 14A and 14B is described in detail hereinbelow. Such a valve, of the electropolished DAD type, is for example derived from a valve marketed by the company NUPRO and manufactured by the company SWAGELOK.

Figure 2:
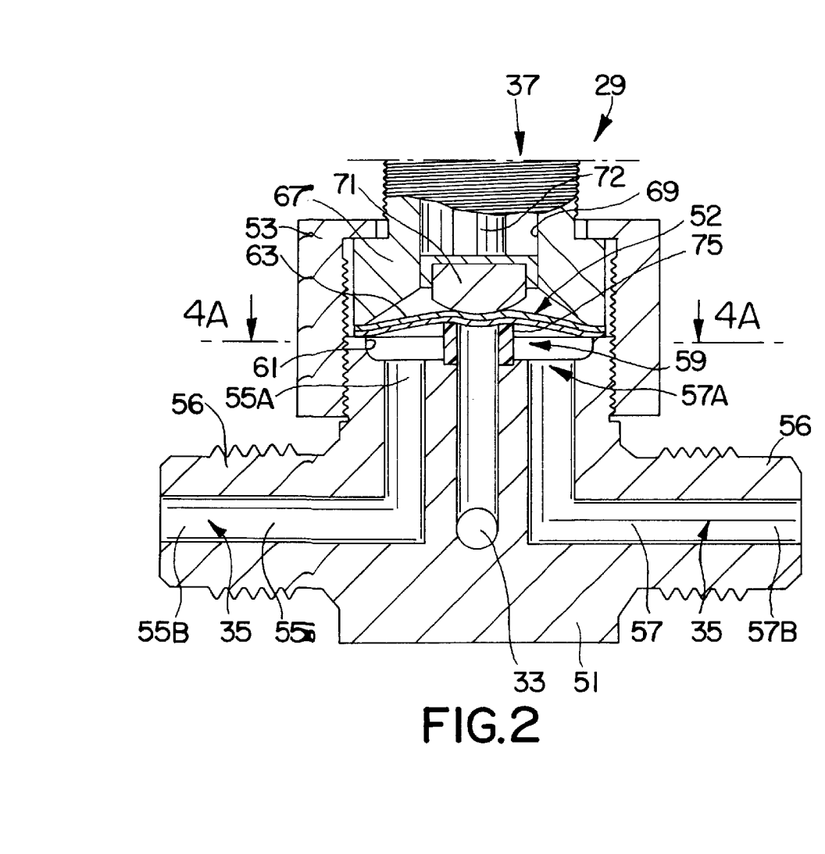
FIG. 2 is a sectional view of a valve of the regulating device in FIG. 1 as well as of a valve of a purification unit in FIG. 1, in the isolating position.
Figure 3:
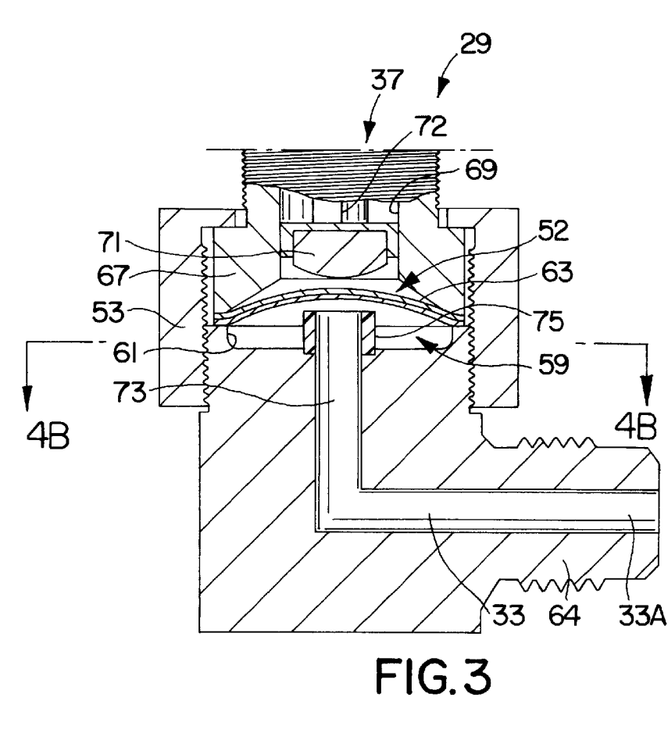
FIG. 3 is a sectional view, of the valve in the communicating position.

As shown in FIGS. 2 and 3, the valve 29 includes a body 51, in which the first conduit 33 and the second conduit 35 are made, a closure member 52 and an actuator 37, shown in part, which screwed onto the body 51 by means of a nut 53.

The second conduit 35 (FIG. 2) is formed by two conduit sections 55 and 57 and by an axisymmetric annular chamber 59. Emerging in a lateral part of the bottom of this chamber 59 is one 55A, 57A of the two ends of each conduit section 55, 57.

The other end, 55B, 57B of each conduit section 55, 57 emerges in a respective lateral connector 56 on the body 51. These ends 55B and 57B are diametrically opposed. The two connectors 56 are intended to be connected to the analyzing line 7, with regard to the regulating device 14A and to the feed line 85, with regard to the regulating device 14B.

The chamber 59 is formed by a substantially cylindrical recess 61, made in the upper face of the body 51, and by the closure member 52. This closure member itself consists of a combination of two diaphragms 63 joined together, these diaphragms covering the recess 61 and constituting the upper wall of the chamber 59.

The diaphragms 63 are made of an elastically deformable material, for example metal. Each diaphragm 63 is a disc, the central part of which is domed in a direction away from the body 51. The edge of the diaphragms 63 is clamped in a sealed manner between the annular edge of the recess 61 and an annular edge of a holding piece 67 which forms part of the actuator 37. The piece 67 is made in the form of a dish so as to allow movement of the domed part of the diaphragms 63.

In its central part opposite the diaphragms 63, the holding piece 67 includes a guide bore 69 in which a pusher 71 driven by a rod 72 of the actuator 37 can slide.

The first conduit 33 of the valve 29 comprises a single straight blind hole, which extends perpendicularly to the axis defined by the ends 55B, 57B of the conduit sections 55, 57, and a connecting duct 73 which emerges at the center of the recess 61.

One end, 33A, of the first conduit 33 emerges in a respective lateral connector 64 on the body 51 and is intended to be connected to the bypass line 31 in the case of the device 14A or to the bypass line 91 in the case of the device 14B.

The end of the duct 73 emerging in the recess 61 includes a cylindrical seal 75 which is forcibly fitted into the body 51 of the valve and which projects into the chamber 59.

Figure 4A:
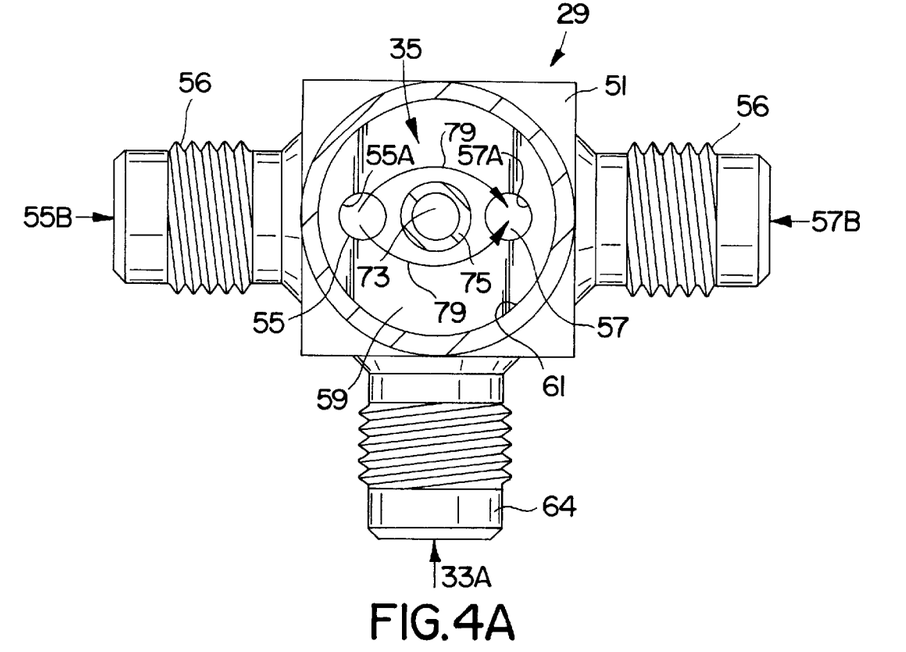
FIG. 4A is a sectional view, along the line 4A—4A in FIG. 2, of the valve in the isolating position.

FIGS. 2 and 4A show the valve 29 in the position for isolating the first conduit 33 from the second conduit 35. In such a case, the central part of the diaphragms 63 is compressed in a sealed manner by the pusher 71 onto the seal 75 so that the duct 73 is isolated from the chamber 59.

Nevertheless, a gas introduced into the second conduit 35 of the valve flows freely, for example from the conduit section 55 into the chamber 59 and then into the conduit section 57, as shown by the arrows 79 in FIG. 4A. It is clear that the second conduit 35 of the valve thus formed has no flow-stagnation volume.

Figure 4B:
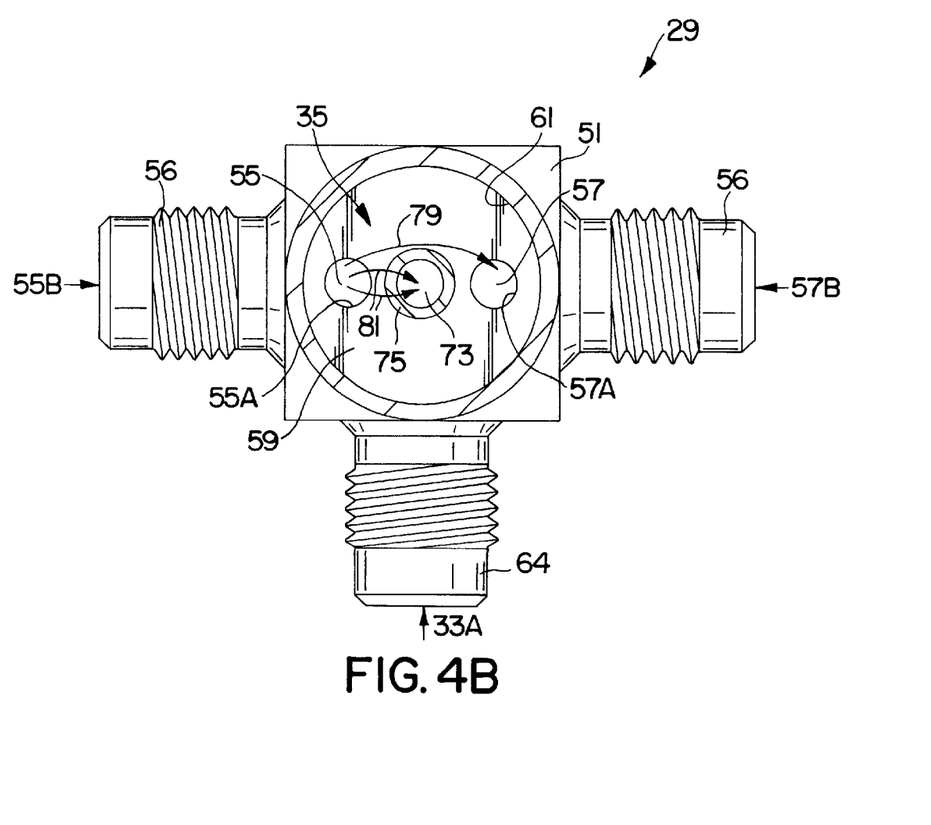
FIG. 4B is a sectional view, along the line 4B—4B in FIG. 3, of the valve in the communicating position.

FIG. 3 and FIG. 4B correspond to a position for bringing the first conduit 33 into communication with the second conduit 35. In such a case, the pusher 71 is set back. The diaphragms 63 resume their initial domed shape by virtue of their spring force. Consequently, a free space is formed between the diaphragms 63 and the seal 75 so that the gas flowing in the second conduit 35 flows away largely via the duct 73 into the first conduit 33, as shown by the arrows 81 in FIG. 4B.

I.3. Operation of the Regulating Device

The operation of the regulating devices 14A, 14B are explained hereinbelow with regard to FIG. 1. For this purpose, two operating methods will be distinguished.

In a first operating mode, the pressure upstream of the regulating device is imposed and the flow rate must be approximately the same for two gases having substantially different molar masses. This operating mode corresponds to the device 14A placed in the analyzing line 7.

In a second operating mode, the gas-flow rate upstream of the regulating device is imposed and it is desired to establish a sonic flow regime or a near-sonic regime. This operating mode corresponds to that produced by the regulating device 14B.

I.3.1. Imposed Pressure Operation

For a light gas, such as hydrogen for example, the valve 29 of the regulating device 14A is switched into the position for isolating the first conduit 33 from the second conduit 35. The gas from the source 5 flows freely in the analyzing line 7 through the second conduit 35 and the orifice 27. In the case of a flow in sonic regime, that is to say in the case in which the ratio between the pressure upstream of the orifice 27 and the pressure downstream of this orifice is greater than 2, it is known that the volume flow rate $D_{27}$ of the gas through the orifice 27 is equal to:

$$D_{27} = K \times P \times S_{27} \times M^{-\frac{1}{2}}$$

where:

P = pressure upstream of the orifice 27, $S_{27}$ = cross section of the orifice 27, M = molar mass of the gas flowing through the orifice, and K = constant which depends on the temperature and nature of the gases.

By virtue of the fact that the conduit 35 of the valve 29 has no flow-stagnation volume and that the orifice 41 of the bypass line 31 is placed close to the end 39 of this line, the regulating device 14A introduces only a negligible flow-stagnation volume into the analyzing line 7 in the position for isolating the first conduit 33 from the second conduit 35 of the valve.

In the case of a gas having a greater molar mass, such as $N_2$ for example, for the same pressure the flow rate through the orifice 27 falls proportionally to the square root of the ratio of the molar masses of the two gases, for example in the case of $N_2$ and $H_2$, to approximately one quarter of the flow rate obtained in the case of $H_2$. In this case, in order to maintain the flow rate delivered by the analyzing line 7 at approximately the same level as the flow rate of a gas of low molar mass, the valve 29 is switched to the state for bringing the first conduit 33 into communication with the second conduit 35. The gas then flows not only through the orifice 27 but also into the bypass line 31 through the orifice 41.

To the flow rate $D_{27}$ is then added, at the connection of the analyzing line 7 and the bypass line 31, the flow rate $D_{41}$ which is given, in sonic regime, by the equation:

$$D_{41} = K \times P \times S_{41} \times M^{-\frac{1}{2}}$$

The nomenclature used is analogous to that used for the flow rate $D_{27}$.

In order for the flow rate controlled by the regulating device 14A to be approximately equal in the case of two gases having respectively a molar mass $M_1$ and $M_2$, the cross section $S_{41}$ of the orifice 41 is chosen in such a way that it satisfies the equation:

$$S_{41} = ((M_1^{1/2}/M_2^{1/2}) \times S_{27}) - S_{27}$$

where $M_1$ is the molar mass of a gas having a high molar mass, and $M_2$ is the molar mass of a gas having a low molar mass.

Preferably, the cross section $S_{41}$ of the orifice 41 is chosen in such a way that the flow rate of $H_2$ in the isolating state of the valve 29 is comparable to the flow rate of $N_2$ through the orifice 27 and the orifice 41 in the communicating state of the valve 29.

I.3.2. Imposed-Flow-Rate Operation

This operating mode of the regulating device is most particularly beneficial in the case in which the flow rate upstream of the regulating device is imposed and in which it is necessary to establish a sonic regime or a near-sonic regime for flow-regulating orifices, such as, for example, those of the flow-splitting means 19. The gas flow rate upstream of the regulating device 14B is imposed by the flow regulator 18.

It will be understood here that the "sonic" regime is preferred and that the fact of departing too far therefrom quite simply makes it difficult to calculate the flow distribution. It is therefore a question of finding a ratio of the upstream and downstream flow rates lying between 1.5 and 30.

In order to explain the imposed-flow-rate operation, it will be assumed that only the regulating device 14B alone placed in the feed line 85, as was described with regard to the device 14A. In the case in which the device 14B is placed in the flow-splitting means 19, the reasoning presented above applies correspondingly.

With a volume flow rate imposed, the pressure upstream of the orifice 27 in the isolating position of the valve 29 is given by the equation:

$$P = K' \times D_{18} \times M^{1/2} \times S_{83}^{-1}$$

with:

$D_{18}$ = volume flow rate imposed by the flow regulator 18,

K' = a constant which depends on the nature of the gas and on the temperature, $S_{27}$ = the cross section of the orifice 27.

The cross section of the orifice 27 is dimensioned in such a way that, for a light gas such as $H_2$, sonic conditions are attained upstream of the orifice 27.

In the case of a gas, such as $N_2$, having a high molar mass, the pressure upstream of the orifice 27, for the same flow rate, is approximately four times greater compared to the upstream pressure obtained in the case of $H_2$.

This is why the valve 29 is switched to the state for bringing the first conduit 33 into communication with the second conduit 35. The gas then flows not only through the orifice 27 but also through the orifice 41. The pressure upstream of the orifice 27 and of the orifice 41 is given by the equation $$P = K' \times D_{18} \times M^{1/2} \times (S_{27} + S_{41})^{-1}$$

with:

$S_{41}$ = cross section of the orifice 41.

In order for the pressure upstream of the regulating device 14B to attain sonic conditions for two gases of different molar mass, the cross section $S_{41}$ of the orifice 41 is chosen in such a way that it satisfies the equation $S_{41}=((M_1^{1/2}/M_2^{1/2})\times S_{27})-S_{27}$ where $M_1$ is the molar mass of a gas of high molar mass and $M_2$ is the molar mass of a gas having a low molar mass.

Of course, instead of the orifices 27 and 41 it is possible to use any gaged restrictions, such as, for example, capillaries, or frits.

Moreover, provision may be made to use diaphragm valves 29 which include means for driving the actuator 37 between the communicating and isolating positions, such as pneumatic valves or electromagnetically-operated valves. The means for controlling the movement of the actuator of the valve are then connected to a control unit, such as a microcomputer or a controller, for example.

II. Device for Delivering a Pure Gas Charged with a Predetermined Quantity of Gaseous Impurities The various units of the device 9 for delivering a pure gas charged with a predetermined quantity of gaseous impurities, namely the purification unit 17, the source of impurities 15 and the means 16 of diluting the impurities in the pure gas in a predetermined manner, are presented in detail hereinbelow.

II.1. Purification Unit

II.1.1. Structure of the Purification Unit

The purification unit 17 comprises an inlet line 160 and a line 162 for delivering a pure gas, between which are placed in parallel three purifiers 164, 166, 168, such as a nitrogen purifier, a hydrogen purifier and an argon/helium purifier, for example.

The inlet of each purifier is joined via a branching valve 170, 172, 174 to the inlet line 160. The outlet of each purifier 164, 166, 168 is connected to the delivery line 162 of the purification unit 17 by means of a valve 176, 178, 180 for supplying the circuit with the purified gas.

The valves 170 to 180 are identical to the valves 29 of the regulating devices 14A, 14B.

Thus, each branching valve 170, 172, 174, as well as each valve 176, 178, 180 for supplying the circuit with the purified gas, comprises a first conduit 33 permanently connected at one end to a corresponding purifier 164, 166, 168. The second conduits 35 of the branching valves 170, 172, 174 are placed in the inlet line 160. The second conduits 35 of the valves 176, 178, 180 for supplying the circuit with the pure gas are placed in the delivery line 162.

The feed line 160 is connected, downstream of the valve 174, to a purge line 182 in which an element 184 for creating a pressure drop, such as a gaged orifice, is placed.

The outlet line 162 is connected, at the end opposite the diluting means 16, to an associated purge line 186 in which an element for creating a pressure drop 188, such as a gaged orifice, is placed.

The purge lines 182 and 186 come together into a common purge line 190 downstream of the gaged orifices 184 and 188.

II.1.2. Operation of the Purification Unit

Depending on the kind of gas which is output by the source 5, the inlet valve 170 of the purifier 164 associated with this gas and the valve 176 of the corresponding outlet are, for example, switched to the state for bringing the conduits 33 and 35 into communication with each other. The gas to be analyzed from the source 5 flows freely through the purifier 164, which purifies this gas. The other valves 172, 174, 178 and 180 are in the isolating state.

If the nature of the gas output by the pressure source 5 is changed, the valves 170, 176 of which hitherto were open, are switched to the isolating state and the valves associated with another purifier are switched to the communicating state.

By virtue of the construction of the valves 170 to 180 and by virtue of the orifices allowing a leakage flow, the feed line 160 and the outlet line 162 are continuously purged. This purification unit 9 furthermore has the advantage that it can be used with various kinds of gases to be purified and that it is virtually free of flow-stagnation volumes.

Advantageously, in order to switch the valves, diaphragm valves are used which include means for controlling the switching of the actuator between the communicating and isolating positions, such as pneumatic or electromagnetically-operated valves for example. The means for controlling the movement of the actuator of each valve are connected to a control unit, such as a microcomputer or a logic controller for example. This control unit includes switching logic means. These logic means are produced, for example, by a computer program loaded into the microcomputer which excludes the possibility of two purifiers being simultaneously in communication with the feed line 160 and the outlet line 162.

II.2. The Source of Impurities

The source of impurities 15 comprises a reservoir containing a mixture of various kinds of gases such as, for example, $N_2$, $CO_2$, CO, $O_2$, $CH_4$, $H_2$, Ar, Kr, Xe, He, etc. This mixture has been produced in such a way that the volume concentrations of most of the gases in this mixture are of the same order of magnitude.

For safety reasons, the concentration of an inert gas, such as helium for example, is chosen preferably to be much higher than the volume concentration of all the other constituents of the mixture. By virtue of such a composition of the mixture, oxidants, such as $O_2$ or CO, may coexist together with fuels, such as $CH_4$, for example, without their being a risk of the reservoir 15 catching fire or exploding.

In order to know accurately, after dilution, the contents of the trace impurities in the pure gas, the composition of the mixture in the reservoir 15 has been accurately determined beforehand using gas analysis means, such as a gas chromatograph for example. The reservoir 15 may, for example, be a bottle under a high pressure (typically 200 bar).

The gases in the mixture are sampled or introduced into the diluting means 16 via a sampling line 204 into which a downstream pressure regulator 205 is placed. The sampling line 204 emerges in an associated purge line 206 in which a shutoff valve 207 and an element for creating a pressure drop, such as a gaged orifice 208, are placed.

II.3. The Means of Diluting the Gaseous Impurity in the Pure Gas in a Predetermined Manner The diluting means 16 comprise, on the one hand, the means 19 of splitting the flow of pure gas delivered by the feed line 162 at the outlet of the purification unit 17 and, on the other hand, three dilution stages 20, 21, 22 placed in series. A pressure gage 86 is placed in the line 162 upstream of the splitting means.

The splitting means 19 comprise the regulating device 14B and two lines 209, 210, said regulating device and said lines being connected in parallel with the feed line 162. A gaged restriction 211, 212, such as a gaged orifice, is placed in each line 209, 210.

The line from the regulating device 14B as well as the lines 209 and 210 with their respective orifices 211, 212 each form a branch for feeding a corresponding dilution stage 20, 21, 22, with pure gas.

The operation of such flow-splitting means is described in detail in Patent Application FR-A-2714968, owned by the assignee of the present application. This is why this operation will not be described hereinbelow.

Figure 5:
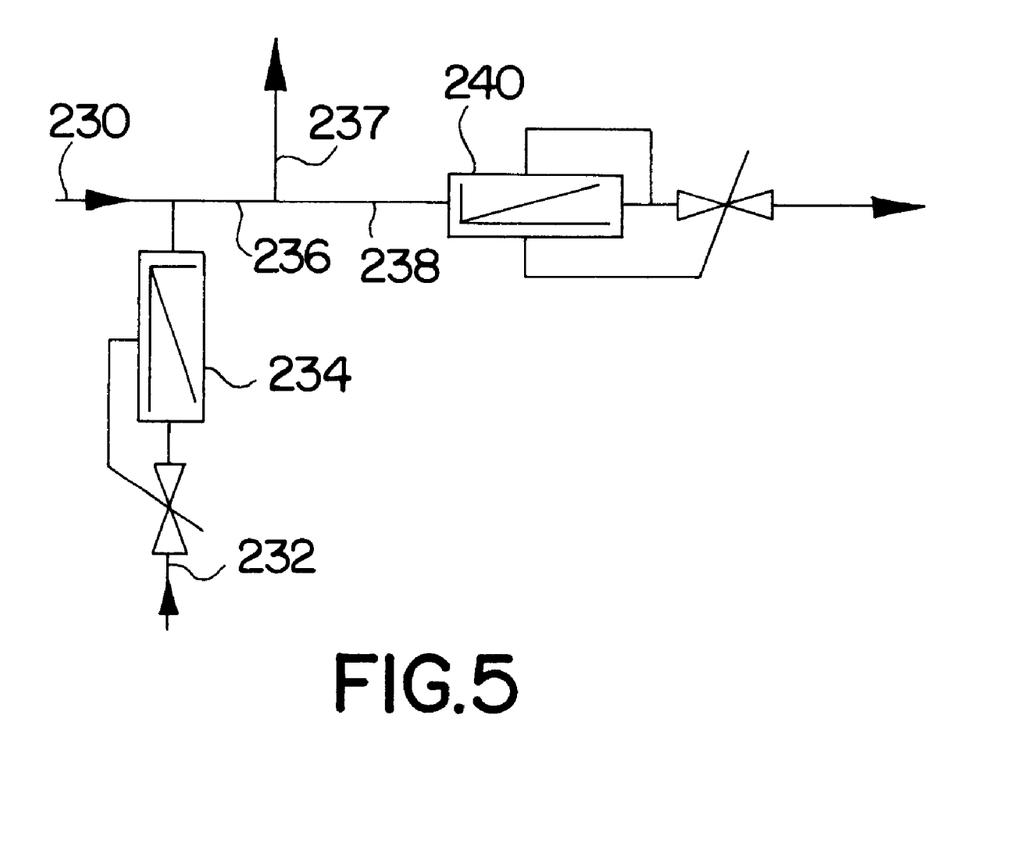
FIG. 5 is a diagram of a dilution stage.

FIG. 5 shows an example of a dilution stage 20, 21 or 22. A dilution stage 20, 21 or 22 comprises a pure gas feed line 230, connected to a corresponding branch of the splitting means 19, and an impurity-containing gas feed line 232.

A mass flow regulator 234 is placed in the feed line 232 so as to enable the degree of dilution of the dilution stage to be varied.

The feed lines 230 and 232 are joined together in such a way that they emerge in a common mixing line 236. The line 236 emerges, on the one hand, in an outlet 237 of the dilution stage. This outlet line 237 is connected to the feed line 232 of the dilution stage placed just downstream.

On the other hand, in the case of the dilution stages 20 and 21, the dilution line 236 is connected to a purge line 238 in which a backpressure regulator 240 is placed. The pressure of a backpressure regulator in one dilution stage is set in such a way that, on the one hand, the sonic conditions for the diluting means are preferably satisfied and, on the other hand, the pressure set is slightly higher than the pressure set in the backpressure regulator placed in a dilution stage downstream, so as to ensure that the gases flow toward the analyzer 3.

The feed line 232 of the dilution stage 20 is joined, downstream of the pressure regulator 205 and upstream of the shutoff valve 207, to the sampling line 204.

The outlet line 237 of the final dilution stage 22 emerges in the outlet line 10 of the delivery device 9, downstream of the regulating device 14B.

The flows at the inlet of each dilution stage are set in such a way that a dilution, for example, of approximately 1/1000 of the gas output by the line 232 in the pure gas output by the line 230 is obtained.

Of course, the "zero" impurity quantity is also a predetermined quantity of trace impurities which the device has to deliver to the analyzer 3. This is why the feed line 232 of the final dilution stage 22 includes a bypass line 242 in which a mass flow regulator 244 is placed.

The outlet line 10 of the delivery device 9 outputs a pure gas in the case in which the regulator 244 is set to a flow rate greater than that of the regulator 234 of the dilution stage 22 and it outputs a pure gas charged with a predetermined quantity of trace impurities in the case in which the flow rate controlled by the regulator 244 is less than that of the regulator 234.

The impurity $H_2O$ is generated for example by a permeation cartridge 250 outputting approximately 250 ng/min and connected as a branch off the pure gas line 230 of the second dilution stage 21.

This permeation cartridge contains water heated here to approximately 50° C. and includes, at one end, a silicone membrane through which the $H_2O$ molecule diffuses.

It will be noted that the cartridge could be placed on the first stage for a higher permeation rate, the permeation rate being chosen to generate in the line a content equivalent to that of the gaseous impurities present at this level of dilution.

Table 1 below shows, for a predetermined composition of the gas mixture in the reservoir 15, two examples of manufacture of a pure gas charged with a predetermined quantity of trace impurities which is output by the outlet line 10 of the delivery device 9, these examples being made in one case with hydrogen as the pure gas and in one case with nitrogen as the pure gas.

TABLE 1

| Impurities | Composition of the reservoir in vol. % | Concentration of the impurities, $H_2$ pure gas | Concentration of the impurities, $N_2$ pure gas |
|---|---|---|---|
| $O_2$ | 5% | 0.20 ppb | 1.62 ppb |
| $H_2$ | 5% | — | 1.62 ppb |
| $N_2$ | 5% | 0.20 ppb | — |
| Ar | 5% | 0.20 ppb | 1.62 ppb |
| CO | 5% | 0.20 ppb | 1.62 ppb |
| $CO_2$ | 5% | 0.20 ppb | 1.62 ppb |
| $CH_4$ | 5% | 0.20 ppb | 1.62 ppb |
| Xe | 5% | 0.20 ppb | 1.62 ppb |
| Kr | 5% | 0.20 ppb | 1.62 ppb |
| He | 55% | 2.19 ppb | 17.85 ppb |
| $H_2O$ | permeation cartridge | 0.81 ppb | 1.58 ppb |

By virtue of the fact that the initial composition of the reservoir 15 has been accurately determined beforehand and that these impurities are diluted in a very precise manner, a pure gas containing a precisely known concentration of trace impurities is obtained.

In addition, using the flowmeters 234 in the feed line 232 of each dilution stage 20, 21, 22, it is possible to vary the range of concentrations of the trace impurities by a factor of 100.

By virtue of the fact that the reservoir 15 contains a mixture of several gases, this constitutes trace impurities in various pure gases. Together with the purification unit 17, the generation of a pure gas charged with predetermined quantities of given trace impurities is therefore considerably facilitated by this device.

III. Device for Selecting One of the Two Gases

As has already been described, the device 13 for selecting one of the two gases comprises two feed lines 11, 12, one of which, 11, is connected to the analyzing line 7 and the other, 12, to the outlet line 10 of the delivery device 9.

Each feed line 11, 12 emerges in a respective purge line 300 and 302. The feed lines 11 and 12 are connected together by means of a connecting line 304. The connecting line 304 is connected to the analyzer 3 via a gas delivery line 306. The outlet of the analyzer 3 also emerges in an associated purge line 308. The purge lines 300 and 308 each include a mass flow regulator 310, 312. A backpressure regulator 314 is placed in the purge line 302.

In order to deliver the gas contained in the line 11 to the analyzer 3, the sum of the flow rates $D_{310}+D_{312}$ controlled by the flow regulators 310 and 312 is set to a flow rate which is less than the flow rate $D_{11}$ of the flow output by the line 11. In order to deliver a calibration gas, that is to say either a pure gas or a gas charged with a predetermined quantity of impurities, to the analyzer 3, the flow rate $D_{310}$ of the flow regulator 310 is set so that it is greater than the flow rate $D_{11}$ of the flow coming from the line 11, and the flow rate $D_{312}$ controlled by the flow regulation 312 is set so that it is slightly less than the gas flow rate $D_{12}$ in the line 12. The pressure of the gas introduced into the analyzer 3 is controlled by the backpressure regulator 314 placed in the purge line 302.

Advantageously, by means of such an arrangement, it is possible not only to select, for delivery to the analyzer 3, the gas to be analyzed or the calibration gas, but it is also possible to control parameters relating to the introduction of the gases into the analyzer 3, such as the flow rate and the pressure.

By virtue of the fact that a smaller number of regulating components is used compared with the device described in the aforementioned Patent Application FR-A-2714968, the cost of the plant is considerably reduced. In addition, a reduction in the number of regulating components also means that there is an increase in the accuracy and reliability of the apparatus 3.

We claim:

1. A selection device for delivering one of two gases to an apparatus, comprising:

an apparatus having an inlet and an outlet;

a gas delivery line connected to the inlet of the apparatus;

a first feed line and a second feed line for respectively feeding a first and a second gas;

a first purge line and a second purge line, the first feed line being connected to the first purge line and the second feed line being connected to the second purge line;

a common connection line connecting the first and the second feed lines to the gas delivery line;

an additional purge line connected to the outlet of the apparatus;

a first element, a second element, and a third element for creating a pressure drop disposed in the first, the second, and the additional purge lines, respectively, the first element for creating a pressure drop and the third element for creating a pressure drop being flow-regulating elements, the second element for creating a pressure drop being a backpressure regulator;

wherein the gas delivery line is only connected to the common connection line and to the apparatus.

2. A selection device as set forth in claim 1, further comprising a first device for supplying gas to the first feed line, a second device for supplying gas to the second feed line, and a source of gas for supplying gas to the first device and to the second device.

3. A selection device as set forth in claim 2, wherein the second device includes a device for purifying the gas from the source of gas to create a pure gas.

4. A selection device as set forth in claim 3, wherein the device for purifying gas includes a plurality of purifying devices for purifying different impurities from the gas from the source of gas.

5. A selection device as set forth in claim 2, wherein the second device includes a source of impurities, and a device for diluting the impurities with pure gas to supply gas with a predetermined quantity of impurities to the second feed line.

6. A selection device as set forth in claim 5, wherein the diluting device includes a plurality of dilution stages placed in series.

7. A selection device as set forth in claim 2, wherein the first device includes an analyzing line disposed between the source of gas and the first feed line, and a flow regulating device disposed in the analyzing line.

* * * * *